US011596157B2

(12) United States Patent
Chen

(10) Patent No.: US 11,596,157 B2
(45) Date of Patent: Mar. 7, 2023

(54) METHOD FOR REALIZING BATCH-BASED TRACEABILITY FOR PORK BASED ON QR CODE

(71) Applicant: Jilin University, Jilin (CN)

(72) Inventor: Taibo Chen, Jilin (CN)

(73) Assignee: Jilin University, Changchun (CN)

( * ) Notice: Subject to any disclaimer, the term of this patent is extended or adjusted under 35 U.S.C. 154(b) by 547 days.

(21) Appl. No.: 16/688,218

(22) Filed: Nov. 19, 2019

(65) Prior Publication Data

US 2020/0154722 A1    May 21, 2020

(51) Int. Cl.
| | | |
|---|---|---|
| *A22B 5/00* | (2006.01) | |
| *A01K 11/00* | (2006.01) | |
| *G01N 33/12* | (2006.01) | |
| *G06K 17/00* | (2006.01) | |
| *G06Q 10/087* | (2023.01) | |

(52) U.S. Cl.
CPC ............ *A22B 5/007* (2013.01); *A01K 11/006* (2013.01); *G01N 33/12* (2013.01); *G06K 17/0022* (2013.01); *G06Q 10/087* (2013.01)

(58) Field of Classification Search
CPC .................................................. G06K 17/0022
USPC ........................................................ 382/110
See application file for complete search history.

(56) References Cited

U.S. PATENT DOCUMENTS

2016/0343120 A1* 11/2016 Johnson ............... G06Q 10/087

FOREIGN PATENT DOCUMENTS

| CN | 105825386 A | 8/2016 |
|---|---|---|
| CN | 108764946 A | 11/2018 |

* cited by examiner

*Primary Examiner* — Rafferty D Kelly

(57) ABSTRACT

Disclosed is a method for realizing batch-based traceability for pork based on a QR code. Based on the QR code, user information is added to a web address carried by the QR code to realize the traceability for the pork. The method includes: 1) registering basic information of pigs in breeding and brokering processes; 2) printing an initial traceability QR code of a carcass in a slaughtering process; 3) adding user information to the initial traceability QR code in a selling process, and updating the user information to the traceability system; and 4) scanning the traceability QR code to recall data of the traceability system in a catering process to achieve transparent information. The pork and pork products are traced from production process to the selling process.

5 Claims, 4 Drawing Sheets

Implementation 1: Carcasses are directly sold to retailers from slaughterhouse

Implementation 2: Slaughterhouses sell carcasses to retailers

Implementation 3: Retailers sell pork cuts to consumers

Implementation 4: Restaurants purchase pork

METHOD FOR REALIZING BATCH-BASED TRACEABILITY FOR PORK BASED ON QR CODE

CROSS-REFERENCE TO RELATED APPLICATIONS

This application claims the benefit of priority from Chinese Patent Application No. 201811372478.1, filed on Nov. 19, 2018. The content of the aforementioned application, including any intervening amendments thereto, is incorporated herein by reference in its entirety.

TECHNICAL FIELD

This application relates to technology of product traceability, in particular to a method for realizing traceability for pork by scanning and analyzing QR codes to add user information to web addresses of the QR codes, and more particularly to a method for realizing batch-based traceability for pork based on QR codes.

BACKGROUND OF THE INVENTION

Safety of pork and pork products have always been a focus of the food safety, and people have conducted in-depth research on solving food safety problems at the source. In existing techniques, traceability information of involving users cannot be easily recorded for storage in the whole selling process of the pork, and the pork cannot be well traced after it is cut. In this application, information of the involving users is added to the structural web address carried by the QR code of the pork, so that traceability information can be updated to the system via internet for storage and management when the involving users carry out a simple operation, i.e. scanning the QR code. The consumers scan the QR code to obtain more detailed traceability information of the pork.

SUMMARY OF THE INVENTION

The present invention aims to provide a method for realizing batch-based traceability for pork based on QR codes. Information of involving users is added to a structural web address carried by the QR code of the pork to realize traceability for the pork.

The present invention adopts the following technical solutions to achieve above objectives.

Provided is a method for realizing batch-based traceability for pork based on QR codes, comprising analyzing the QR code and adding user information to a web address carried by the QR code to realize traceability for the pork. The users comprise restaurants, retailers, slaughterhouses, pig brokers and pig farm. Specifically, the method comprises the following steps:

1) registering basic information of pigs in a breeding process, and binding information of a pig broker with information of a pig farm/household in a pig brokering process;

wherein traceability information in the breeding process comprises a breeding record, an immunity record and a self-checking record; the pig farm/household logs in and maintains a traceability system, and the traceability system distributes an identification QR code to the pig farm/household; in the pig brokering process, the pig broker scans the unique identification QR code provided by the pig farm/household to acquire the traceability information in the breeding process, and information of the pig broker and information of the pig farm/household are bound; information of a batch of pigs is registered, and the registered information is updated to the traceability system for storage;

when step 1 is completed, the traceability system is stored with the breeding record, the immunity record, the self-checking record, information of corresponding breeding workers and pig brokers;

2) generating an initial traceability QR code of a carcass in a slaughtering process registering admission information and outbound information of the pigs at a slaughterhouse, and printing the initial traceability QR code of the carcass through the traceability system based on a serial number of the slaughterhouse; when registering the outbound information of the pigs, scanning the initial traceability QR code of the carcass by a checkout worker using a scanner to match the carcass with users in the traceability system;

3) adding user information to the initial traceability QR code in a selling process, and updating the user information to the traceability system selling the carcass with the initial traceability QR code from the slaughterhouse to the users which comprises consumers, restaurants and retailers; adding information of the users except for the consumers as a field behind the web address carried by the QR code by scanning the QR code; updating the information loaded in the web address to the traceability system via internet for storage and management;

wherein when the pork is directly bought from the slaughterhouse, the traceability information comprises the breading information and slaughtering information; when the pork is not directly bought from the slaughterhouse and the slaughterhouse thereof is traceable, information field of the retailers are added behind the web address carried by the initial traceability QR code; the consumers scan the QR code on a receipt provided by the retailers to recall data from the traceability system via the internet, so that traceability information of the pork is obtained; and 4) scanning the traceability QR code to recall data of the traceability system in a catering process to achieve transparent information when the consumers ask for the receipt after the pork is bought at the retailers of a farmer's market or a supermarket, the users check a name of the retailers, a weight, price and traceability QR code of the pork on the receipt; the consumers scan the traceability QR code on the receipt through a terminal device, and the traceability information is recalled via the internet so as to view traceability information of the pork in a whole process; wherein the traceability information comprises retailer information, slaughterhouse information and pork quality information in respective processes.

In the step 1, the pig farm/household is involved in the traceability system, and the unique identification QR code is generated by the traceability system; the pig farm/household adds the breeding information and immunity information to the traceability system in the breeding process, when the pig broker collects the pigs in the pig farm/household, the pigs to be slaughtered and the pig farm/household are matched through a tattooing code; information of the batch of the pigs are registered, and the breeding information thereof is obtained by scanning the unique identification QR code of the pig farm/household, so that information of the pig broker and information of the pig farm/household are bound to register pig brokering information; after the pig broker pays the pig farm/household for the pigs, a livestock station issues an animal quarantine certificate for the pig broker, and the pigs are sent to the slaughterhouse.

In the step 2, when the pigs are sent to the slaughterhouse by the pig broker, the admission information of the pigs are registered at the slaughterhouse by scanning an identification QR code of the pig broker or manually filling information of the pig broker; quarantine information of the pigs are registered, and an inspection certificate of origin are updated to the traceability system; the initial traceability QR code of the carcass is printed through the traceability system based on the serial number of the slaughterhouse, and are fixed onto the carcass by a nail gun; storage information are added, by the traceability system, as a field behind the web address carried by the QR code, so that the initial traceability QR code of the carcass contains all registered information before the batch of pigs are slaughtered.

In the step 3, when the carcass with the initial traceability QR code is directly sold to consumers from the slaughterhouse, the consumers scan the initial traceability QR code via the terminal device to obtain the traceability information comprising the breeding information and slaughtering information; when the users except for the consumers scan the initial traceability QR code, the web address is recognized by a background, and the user information is added behind the web address to form an information traceability chain; the added user information is updated into the traceability system via the internet, and the traceability information comprises the breeding information, the slaughtering information and the user information;

when the carcass with the initial traceability QR code is sold to the users through the retailers from the slaughterhouse, the retailers scan the initial traceability QR code of the carcass using an electronic scale which has a scanner gun for identifying the QR code; the electronic scale prints the receipt with the QR code, and information of the retailers and selling information are added behind the web address carried by the QR code; the QR code is scanned to acquire pork information by recalling data of the traceability system through the internet; at this time, the traceability information comprises the breeding information, the slaughtering information, retailer information; when the retailers sell the carcass to the restaurants, the restaurants are required to scan the QR code on the carcass of the retailer, so that pork information and traceability information are obtained by recalling the data of the traceability system via the internet, and the web address are identified by the background; information of the restaurants comprising purchasing information is added behind the web address, and the information of the restaurants are updated into the traceability system; at this time, the traceability information comprises the breeding information, the slaughtering information, the retailer information and restaurant information;

when selling the carcass, if the retailers need to cut the carcass into pork cuts, a primary retailer scans the QR code of the carcass using the electronic scale which has the scanner for identifying the QR code, and a receipt of the carcass is printed; when purchasing the pork cuts, secondary, third . . . n-th retailers scan the QR code on the receipt printed by the previous retailer, and at the same time, the web address carried by the QR code is added with the field according to tree structure coding rules, so that the pork cuts are traceable; after the pork cuts are sold, the electronic scale automatically updates selling data of the pork cuts to the traceability system to form a complete account; when getting the receipt, the consumers scan the QR code on the receipt to inquire the traceability information comprising the breeding information, slaughtering information and selling information.

The present invention has the following beneficial effects. The method of the present invention realizes quality traceability for pork and pork products in a whole process by scanning the QR code, thus solving the safety problem of the pork and pork products in the source. Especially, the user information is added to the structural web address carried by the QR code of the pork, so that the involving users are not required to manually record massive information with complicated operations, and they only need to scan the QR code to record and update the traceability information of the pork. In addition, after a cutting process, the pork and pork products can also achieve an excellent traceability effect.

The pork and pork products are traced from production process to the selling process, thus processing animal products which are high-quality and safe at the source. By this method, the source and flow of the pork and pork products are traceable, and information thereof can be inquired, and the person who needs to take responsibility can be found out. The pork from the slaughterhouse can be traced when users inquire the traceability information thereof through the scan function in the terminal device. In this method, one object corresponds to one QR code and can be traced in the whole process, and safety problems of the pork and pork products are solved at the source, which is of strong practicability.

BRIEF DESCRIPTION OF THE DRAWINGS

The companying drawings described herein are used to better illustrate the present invention and constitute a part of this application. The embodiments described herein are only illustrative, and are not intended to limit the scope of the present invention.

DETAILED DESCRIPTION OF EMBODIMENTS

The present invention is further illustrated in detail with reference to the accompanying drawings and embodiments.

Figure 1A:
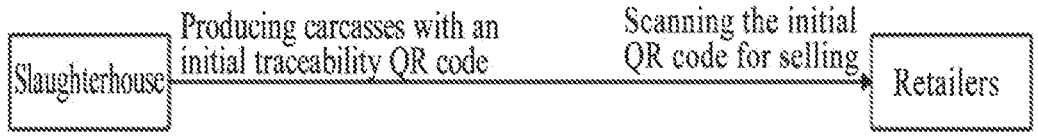
FIGS. 1A-D are flow charts showing various implementations of a method for realizing batch-based traceability for pork based on QR codes according to the present invention under different instances.
Figure 1B:
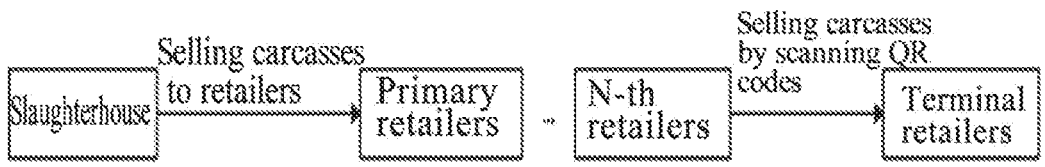
Figure 1C:
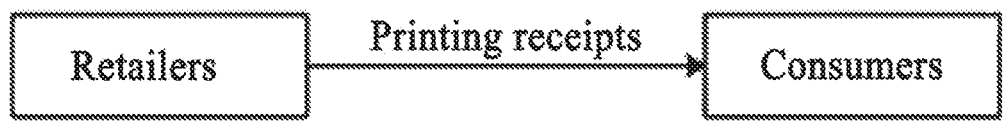
Figure 1D:
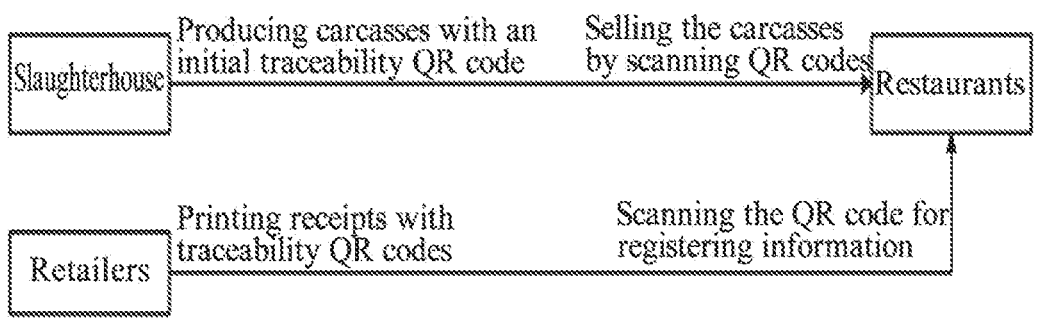
Figure 2A:
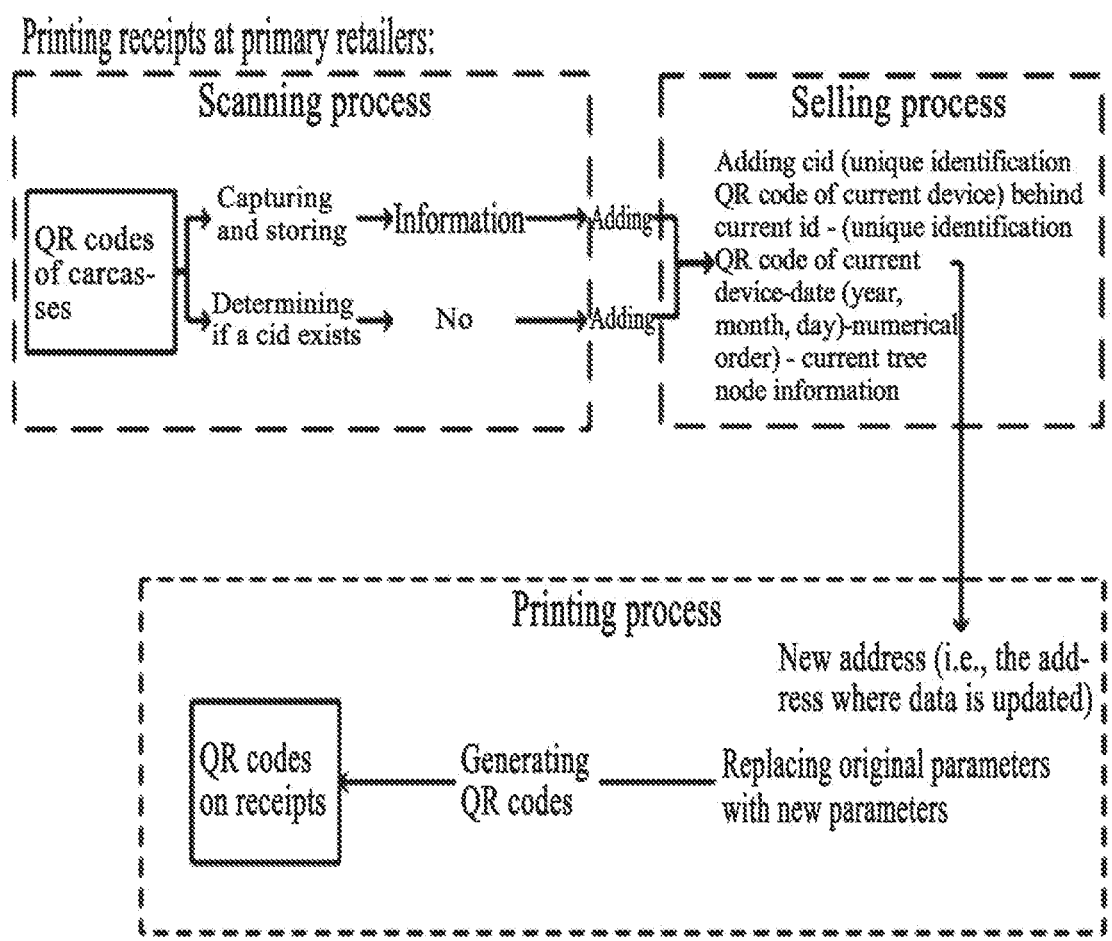
FIGS. 2A-B are flow charts of generating a QR code on a receipt provided by a primary retailer and secondary retailer.
Figure 2B:
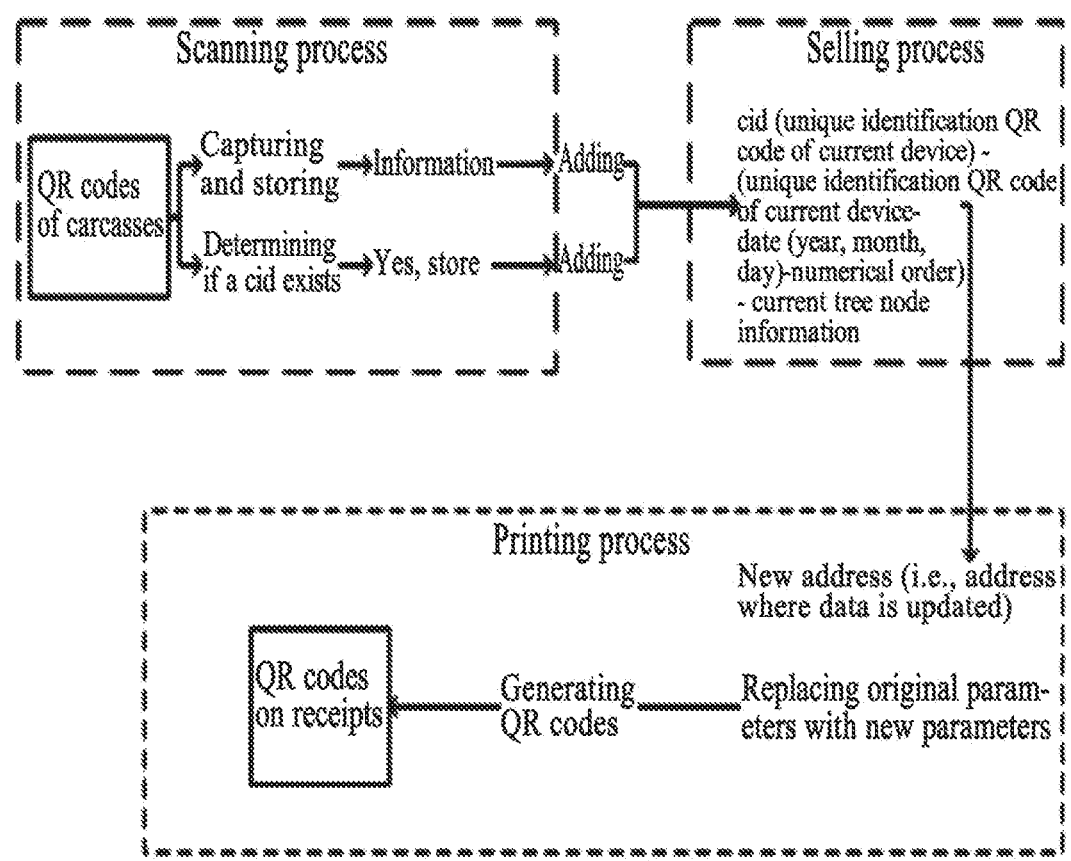
Figure 3:
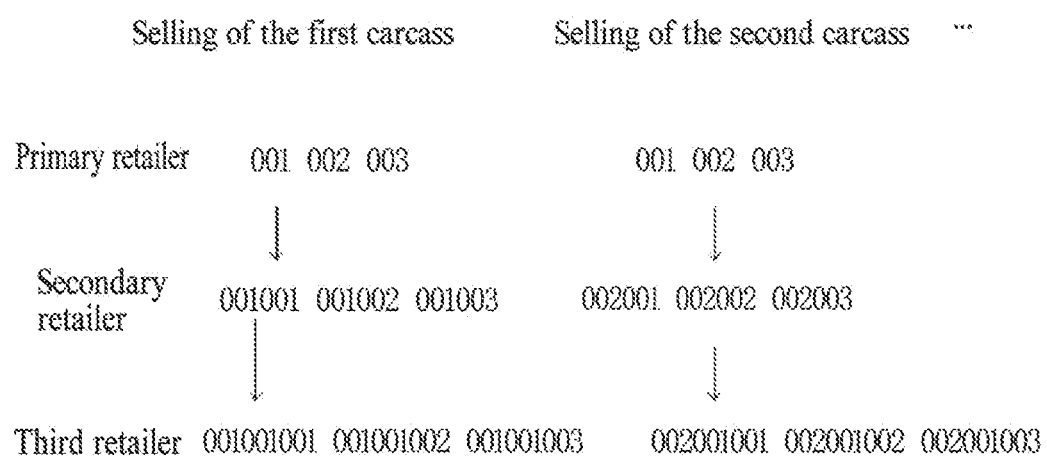
FIG. 3 is a tree diagram showing, by way of example, the process of generating the QR code, for tracing information of pork cuts according to the present invention.

As shown in FIGS. 1-3, illustrated is a method for realizing batch-based traceability for pork based on QR codes. Based on the QR code, user information is added to a web address carried by the QR code to realize traceability for the pork. The method comprises the following steps.

1) Basic information of pigs is registered in a breeding process, and information of a pig broker is bound with information of a pig farm/household in a pig brokering process.

The pig farm/household is involved in the traceability system, in which an identification QR code is distributed to the pig farm/household; in the breeding process, the pig farm/household adds the breeding information and the immunity information to the traceability system in the pig breeding process.

When the pig broker collects the pigs in the pig farm/household, the pigs to be slaughtered and the pig farm/household are matched through a tattooing code; information of the batch of the pigs are registered, and the breeding information thereof is obtained by scanning the unique identification QR code of the pig farm/household, so that information of the pig broker and information of the pig farm/household are bound; pig farm/household numerals (i.e., tattooing codes), registration number, the number and gross weight of the pigs are filled to register pig brokering information; after the pig broker pays the pig farm/household for the pigs, a livestock station issues an animal quarantine certificate (animal A/B) for the pig broker, and the pigs are sent to the slaughterhouse.

When step 1 is completed, the traceability system is stored with the breeding record, the immunity record, the self-checking record, information of corresponding breeding workers and pig brokers.

2) An initial traceability QR code of a carcass is generated in a slaughtering process.

Admission information and outbound information of the pigs are registered at a slaughterhouse, and the initial traceability QR code of the carcass are printed through the traceability system based on a serial number of the slaughterhouse. When the pigs are sent to the slaughterhouse by the pig broker, the admission information of the pigs are registered at the slaughterhouse by scanning an identification QR code of the pig broker or manually filling information of the pig broker; quarantine information of the pigs are registered, and an inspection certificate of origin are updated to the traceability system; the initial traceability QR code of the carcass is printed through the traceability system based on the serial number of the slaughterhouse, and are fixed onto the carcass by a nail gun; storage information are added, by the traceability system, as a field behind the web address carried by the QR code, so that the initial traceability QR code of the carcass contains all registered information before the batch of pigs are slaughtered.

When registering the outbound information of the pigs, the checkout workers scan the initial traceability QR code of the carcass using a scanner to match the carcass with users in the traceability system.

3) User information is added to the initial traceability QR code in a selling process, and the user information is updated to the traceability system.

When the carcass with the initial traceability QR code is directly sold to users from the slaughterhouse, the users scan the initial traceability QR code via the terminal device to obtain the traceability information comprising the breeding information and slaughtering information; when the users except for the consumers scan the initial traceability QR code, the web address is recognized by a background, and the user information is added behind the web address to form an information traceability chain; the added user information is updated into the traceability system via the internet, and the traceability information comprises the breeding information, the slaughtering information and the user information.

When the carcass with the initial traceability QR code is sold to the users through the retailers from the slaughterhouse, the retailers scan the initial traceability QR code of the carcass using an electronic scale which has a scanner gun for identifying the QR code; the electronic scale prints the receipt with the QR code, and information of the retailers and selling information are added behind the web address carried by the QR code; the QR code is scanned to acquire pork information by recalling data of the traceability system through the internet; at this time, the traceability information comprises the breeding information, the slaughtering information, retailer information; when the retailers sell the carcass to the restaurants, the restaurants are required to scan the QR code on the carcass of the retailers, so that pork information and traceability information are obtained by recalling the data of the traceability system via the internet, and the web address are identified by the background; information of the restaurants comprising purchasing information is added behind the web address, and the information of the restaurants are updated into the traceability system; at this time, the traceability information comprises the breeding information, the slaughtering information, the retailer information and restaurant information.

As shown in FIG. 3, when selling the carcass, if the retailers need to cut the carcass into pork cuts, a primary retailer scans the QR code of the carcass using the electronic scale which has the scanner for identifying the QR code, and a receipt of the carcass is printed; when purchasing the pork cuts, secondary, third, . . . n-th retailers scan the QR code on the receipt printed by the previous retailer, and at the same time, the web address carried by the QR code is added with the field according to tree structure coding rules, so that the pork cuts are traceable; after the pork cuts are sold, the electronic scale automatically updates selling data of the pork cuts to the traceability system to form a complete account; when getting the receipt, the users scan the QR code on the receipt to inquire the traceability information comprising the breeding information, slaughtering information and selling information.

4) The traceability QR code is scanned to recall data of the traceability system in a catering process to achieve transparent information.

When the consumers ask for the receipt after the pork is bought at the retailers of a farmer's market or a supermarket, the users check a name of the retailers, a weight, price and traceability QR code of the pork on the receipt; the consumers scan the traceability QR code on the receipt through a terminal device, and the traceability information is recalled via the internet so as to view traceability information of the pork in a whole process; the traceability information comprises retailer information, slaughterhouse information and pork quality information in respective processes.

The above embodiment is only for illustration and is not intended to limit the scope of the present invention. Various modifications and changes of the present invention can be made by those skilled in the art, and any modification, equivalent replacement, or improvement made to the present invention shall fall within the scope of the present invention.

I claim:

1. A method for realizing batch-based traceability for pork, comprising:
   a) registering and storing on a traceability system basic pig information for pigs during a breeding process, wherein the basic pig information comprises a breeding record, an immunity record and a self-checking record; and distributing, by the traceability system, an identification QR code to each of the pigs bred in a pig farm or a pig household;
   b) scanning the identification QR code distributed to each of the pigs from the pig farm or pig household to acquire the basic pig information during the breeding process; and combining pig broker information during a pig brokering process to update the basic pig information on the traceability system;
   c) registering on the traceability system slaughtering information during a slaughtering process to generate a traceability QR code for the pork through the traceability system; wherein the slaughtering information comprises admission information for the pigs from the pig broker and outbound information for pork obtained from the pigs in a slaughterhouse;

d) updating the traceability QR code on the traceability system by adding retailer information during a selling process; and e) scanning, at a terminal device, the traceability QR code to obtain traceability information comprising the retailer information, the slaughtering information, the pig broker information and the basic pig information.

2. The method of claim 1, wherein step a) comprises:
generating, by the traceability system, the identification QR code;
wherein the pig farm or pig household provides the basic pig information comprising the breeding record, the immunity record and the self-checking record.

3. The method of claim 1, wherein step c) comprises:
sending the pigs from the pig broker to the slaughterhouse;
updating the basic pig information on the traceability system by adding the outbound information for pork to generate the traceability QR code; wherein the outbound information for pork comprises quarantine information, inspection certificate of origin and storage information; and
attaching the traceability QR code onto the pork.

4. The method of claim 1, wherein step d) comprises:
linking a web address to the traceability QR code and scanning the traceability QR code to visit the web address that displays the basic pig information, the pig broker information and the slaughtering information; and
adding the retailer information on the web address and updating the traceability QR code on the traceability system.

5. The method of claim 1, further comprising: repeating step d) when the retailer comprises a plurality of retailers.

* * * * *